United States Patent [19]

Meine et al.

[11] Patent Number: 6,121,227
[45] Date of Patent: Sep. 19, 2000

[54] LIQUID DETERGENT

[75] Inventors: Georg Meine, Mettmann; Rolf Puchta, Haan; Juergen Hoffmeister, Duesseldorf, all of Germany

[73] Assignee: Henkel Kommanditgesellschaft Auf Aktien, Duesseldorf, Germany

[21] Appl. No.: 08/094,072

[22] PCT Filed: Dec. 17, 1991

[86] PCT No.: PCT/EP91/02428

§ 371 Date: Jul. 28, 1993

§ 102(e) Date: Jul. 28, 1993

[87] PCT Pub. No.: WO92/13055

PCT Pub. Date: Aug. 6, 1992

[30] Foreign Application Priority Data

Jan. 29, 1991 [DE] Germany ............................ 41 02 502

[51] Int. Cl.$^7$ ........................... C11D 17/00; C11D 17/08; C11D 3/00; C11D 7/42
[52] U.S. Cl. ........................ 510/416; 510/221; 510/226; 510/320; 510/321; 510/337; 510/340; 510/342; 510/351; 510/421; 510/422; 510/428; 510/470; 510/481; 510/498
[58] Field of Search ...................................... 252/108, 121, 252/122, 550, 174.17, 174.18

[56] References Cited

U.S. PATENT DOCUMENTS

| 4,285,841 | 8/1981 | Barrat et al. | 252/559 |
| 4,507,219 | 3/1985 | Hughes | 252/552 |
| 5,244,593 | 9/1993 | Roselle et al. | 252/100 |
| 5,258,142 | 11/1993 | Giesen et al. | 252/174.17 |

FOREIGN PATENT DOCUMENTS

| 0070074 | 1/1983 | European Pat. Off. | C11D 1/83 |
| 0388810 | 9/1990 | European Pat. Off. . | |
| 0403948 | 12/1990 | European Pat. Off. . | |
| 3920480 | 1/1991 | Germany | C11D 17/08 |
| 9203527 | 3/1992 | WIPO . | |

*Primary Examiner*—Mark L. Bell
*Assistant Examiner*—Patricia L. Hailey
*Attorney, Agent, or Firm*—Henry E. Millson, Jr.; John E. Drach; Glenn E. J. Murphy

[57] ABSTRACT

A storable, high-viscosity liquid detergent having high washing power and pronounced foaming comprising water, and from about 2% to about 10% by weight of a fatty alcohol sulfate, from about 5% to 25% by weight of an alkyl polyglycoside; from about 0.1% to about 9% by weight of a soap; and from about 3% to 8% by weight of a lower alcohol, wherein said detergent has a viscosity of from about 500 mPa's to about 3000 mPa's.

20 Claims, No Drawings

LIQUID DETERGENT

BACKGROUND OF THE INVENTION

This invention relates to a storable, highviscosity liquid detergent.

STATEMENT OF RELATED ART

In recent years, liquid detergents have been enjoying increasing popularity among consumers because they have certain advantages over powder-form detergents in terms of handling and are capable of more effectively removing greasy and oily soil. This particular advantage is attributable to the fact that liquid detergents can contain relatively large quantities of nonionic surfactants which are particularly effective against greasy or oily soil. The consumer expects such detergents to be available in highly concentrated form, so that they may be dispensed in relatively small quantities by comparison with powder-form detergents, and to have a certain consistency. This consistency is equated with a high active-substance content. This applies not only to laundry detergents, but also to shampoos, manual wash detergents, dishwashing detergents and cosmetic preparations. Accordingly, the term "liquid detergent" is used hereinafter for the products mentioned, but especially for detergents for delicate fabrics and for shampoos.

To ensure stability in storage, even over prolonged periods, liquid detergents generally contain preservatives which occasionally have unwanted side effects. In addition to good washing power, the liquid detergents mentioned are also expected to show pronounced foaming, although on the other hand it is important that the foam can also be easily rinsed out by the consumer.

Accordingly, there has been no shortage of attempts to provide liquid detergents which correspond to consumer demands in regard to their washing effect, their foaming behavior, their stability in storage and their handling by using new surfactant combinations, foam regulators and preservatives. Accordingly, the problem addressed by the present invention was also to provide a liquid detergent combining good washing power with high stability in storage, the composition of the detergent being such that the above-described disadvantages of known products would be avoided.

EP-A-70 074 describes surfactant combinations containing alkyl polysaccharides and anionic surfactants of the sulfate, sulfonate and/or carboxylate type in certain mixing ratios. In aqueous solution, these surfactant combinations form a stable foam which can be completely removed by rinsing.

It is known that the viscosity of liquid detergents can often be increased by addition of electrolyte. However, the electrolyte itself does not contribute towards the washing result and pollutes the wastewater. In addition, the surfactant system is generally very sensitive to even minor variations in the electrolyte content, so that the quantity of electrolyte to be added always has to be redetermined whenever the raw materials—which in turn generally contain varying amounts of electrolyte—are changed. Accordingly, there has been no shortage of attempts to adjust the viscosity of liquid detergents by a suitable combination of washingactive detergent ingredients. If lower alcohols are added to such liquid detergents to improve their stability in storage, products of very low viscosity are generally obtained. For example, DE-A-39 20 480 describes a liquid detergent containing fatty alcohol sulfate in combination with alkyl polyglycoside and a high percentage of a soap mixture consisting of salts of unsaturated fatty acids and salts of saturated fatty acids in a certain ratio by weight to one another. An addition of lower alcohols to improve the stability of the described detergents in storage leads to products of low viscosity.

Accordingly, the problem addressed by the present invention was to provide storable, high-viscosity liquid detergents combining high washing power with pronounced foaming, the foam generated having to be readily removable by washing.

DESCRIPTION OF THE INVENTION

Accordingly, the present invention relates to a liquid detergent containing anionic surfactant, alkyl polyglycoside and soap, characterized in that it contains 2 to 10% by weight fatty alcohol sulfate 5 to 25% by weight alkyl polyglycoside 0.1 to 9% by weight soap 3 to 8% by weight lower alcohol and has a viscosity of 400 to 3000 mPa·s. Suitable fatty alcohol sulfates are the sulfuric acid monoesters of $C_{10-20}$ and, more particularly, $C_{12-18}$ fatty alcohols, such as lauryl, myristyl or cetyl alcohol, and the sulfuric acid monoesters of fatty alcohol mixtures obtained from coconut oil, palm and palm kernel oil and tallow which may additionally contain unsaturated alcohols, for example oleyl alcohol. Mixtures in which 50 to 70% by weight of the alkyl radicals contain 12 carbon atoms, 18 to 30% by weight 14 carbon atoms, 5 to 15% by weight 16 carbon atoms, less than 3% by weight 10 carbon atoms and less than 10% by weight 18 carbon atoms are preferably used.

Suitable alkyl polyglycosides are compounds having a degree of polymerization (D.P.) of 1.2 to 1.4. The alkyl radical contains 8 to 22 carbon atoms and preferably 12 to 18 carbon atoms. It is derived from lauryl, myristyl, cetyl and stearyl alcohol and from technical fractions preferably containing saturated alcohols. It is particularly preferred to use alkyl glucosides in which 50 to 70% by weight of the alkyl radical contains 12 carbon atoms and 18 to 30% by weight 14 carbon atoms. Alkyl polyglycosides such as these are commerically available substances which are produced by acid-catalyzed reaction of glycosides and fatty alcohol.

The soaps used are the alkali metal or alkanolamine salt of a saturated fatty acid or of a mixture of substantially saturated fatty acids. The potassium salt of $C_{10-20}$ fatty acids is preferably used. A suitable fatty acid is, for example, the potassium salt of coconut oil fatty acid. This soap is preferred.

The alcohol to be used in the liquid detergents according to the invention is preferably an alkanol or an alkanediol containing 1 to 3 carbon atoms. Of these alcohols, ethanol is preferred. The addition of ethanol to the detergents according to the invention ensures excellent stability in storage, even over prolonged periods.

Detergents for delicate fabrics preferably contain 3 to 8% by weight of the soap mentioned above. By contrast, shampoos require a smaller quantity of soap. Particularly balanced properties are shown by a shampoo containing 0.1 to 1.0% by weight soap.

In the production of the liquid detergents mentioned, the soap may be used as such or, alternatively, the corresponding fatty acid and the desired base, preferably potassium hydroxide, may be separately added. The second of these two methods has the advantage that the pH value of the liquid detergent can thus be regulated within certain limits. It may occasionally be advisable for other surfactants to be additionally present in the liquid detergents according to the invention. Suitable other surfactants are, above all, fatty alcohol ethoxylates and also amphoteric surfactants and surfactants of the betaine type. Surfactants such as these may be present in the liquid detergents according to the invention in quantities of up to 8% by weight. In addition, other typical ingredients of liquid detergents, for example pearlescers, dyes, fragrances or enzymes and also builders, may also be present. Liquid detergents according to the present invention have a viscosity of 400 to 3000 mPas at room temperature. It is highly surprising that a viscosity as high as this can be established without thickeners and with a relatively small percentage of soap in the presence of the lower alcohols which improve stability in storage.

EXAMPLES

Example 1

A liquid detergent having the following composition:

5.0% by weight $C_{12-18}$ fatty alcohol sulfate Na 10.0% by weight $C_{12-14}$ alkyl polyglucoside, 1.4

5.0% by weight $C_{12-18}$ coconut oil soap K 5.0% by weight ethanol 1.0% by weight fragrance balance water The molten soap and the fatty alcohol sulfate were stirred into water heated to 80° C. and, after cooling to 50° C., the ethanol and alkyl polyglucoside were mixed in. The fragrance was added after cooling.

This product had a pH value of 8.0 and a viscosity of 840 mPas at room temperature. Its stability in storage was excellent; there was no need for additional preservatives.

Normally soiled domestic washing was washed with this detergent in an automatic drum-type washing machine (AEG 570) in a one-wash cycle for easy-care washing. The hardness of the water was 16° d (d=German hardness) and 120 g detergent were used per machine load. The washing tests were carried out at 30, 40 and 60° C. and the washing effect was determined by visual evaluation and by measurement of the reflection value of the washed fabrics. A high-quality commercially available liquid light-duty detergent was used under the same conditions for comparison. In addition to the washing effect, foam height and foam removal after three wash cycles were evaluated. No significant differences were observed in the performance features of the two detergents.

Surprisingly, viscosity can be increased by reducing the soap content should this be desirable.

Example 2

The controllability of foaming behavior through the soap concentration in the formulations according to the invention may be utilized, for example, to formulate shampoos of relatively high viscosity.

A storable shampoo having the following composition was prepared:

1.0% by weight ethylene glycol stearate 5.0% by weight fatty alcohol sulfate 10.0% by weight alkyl polyglucoside 0.5% by weight soap 5.0% by weight ethanol 1.0% by weight fragrance balance water This shampoo had a viscosity of 1435 mPas and a pH value of 7.9. Foam behavior and removability of the shampoo by rinsing were both excellent and corresponded to those of a high-quality commercial shampoo.

What is claimed is:

1. A liquid detergent comprising water; and from about 2% to about 10% by weight of a fatty alcohol sulfate, from about 5% to about 25% by weight of an alkyl polyglycoside; from about 0.1% to about 9% by weight of a soap; and from about 3% to about 8% by weight of a lower alcohol, wherein said detergent has a viscosity of from about 400 mPa·s to about 3000 mPa·s.

2. A liquid detergent as claimed in claim 1 wherein said soap is the alkali metal or alkanolamine salt of a saturated fatty acid or of a mixture of substantially saturated fatty acids.

3. A liquid detergent as claimed in claim 2 wherein said soap is the potassium salt of a $C_{10-20}$ fatty acid.

4. A liquid detergent as claimed in claim 1 wherein said lower alcohol is an alkanol or alkanediol having from 1 to 3 carbon atoms.

5. A liquid detergent as claimed in claim 4 wherein said alkanol is ethanol.

6. A liquid detergent as claimed in claim 1 wherein the amount of said soap is from about 0.1% to about 8% by weight.

7. A liquid detergent as claimed in claim 6 wherein the amount of said soap is from about 3% to about 8% by weight.

8. A liquid detergent as claimed in claim 1 further comprising an additional nonionic surfactant and/or a cationic surfactant.

9. A liquid detergent as claimed in claim 8 wherein said additional nonionic surfactant is an ethoxylated fatty alcohol.

10. A liquid detergent as claimed in claim 9 wherein said cationic surfactant is a betaine.

11. A liquid detergent as claimed in claim 1 further comprising at least one of a pearlizer, a dye, a fragrance, an enzyme, and a builder.

12. The liquid detergent of claim 1 wherein the fatty alcohol sulfate is a sulfuric acid monoester of a $C_{10-20}$ fatty alcohol.

13. The liquid detergent of claim 12 wherein the alkyl polyglycoside has a degree of polymerization of from about 1.2 to about 1.4 and the alkyl group contains from 8 to 22 carbon atoms.

14. The liquid detergent of claim 11 wherein the alkyl polyglycoside has a degree of polymerization of from about 1.2 to about 1.4 and the alkyl group contains from 8 to 22 carbon atoms.

15. The liquid detergent of claim 11 wherein the fatty alcohol sulfate is a sulfuric acid monoester of a $C_{10-20}$ fatty alcohol; the alkyl polyglycoside has a degree of polymerization of from about 1.2 to about 1.4 and the alkyl group contains from 8 to 22 carbon atoms; the soap is an alkali metal or alkanolamine salt of a saturated fatty acid or of a mixture of substantially saturated fatty acids; and the lower alcohol is an alkanol or alkanediol having from 1 to 3 carbon atoms.

16. The liquid detergent of claim 15 wherein the soap is the potassium salt of a $C_{10-20}$ fatty acid.

17. The liquid detergent of claim 15 wherein the lower alcohol is ethanol.

18. The liquid detergent of claim 15 wherein the liquid detergent also contains at least one of the following: an additional nonionic surfactant, a cationic surfactant, a pearlizer, a dye, a fragrance, an enzyme, and a builder.

19. The liquid detergent of claim 18 wherein the additional nonionoic surfactant is an ethoxylated fatty alcohol, and the additional cationic surfactant is a betaine.

20. A shampoo composition comprising water; and from about 2% to about 10% by weight of a fatty alcohol sulfate, from about 5% to about 25% by weight of an alkyl polyglycoside; from about 0.1% to about 1.0% by weight of a soap; and from about 3% to about 8% by weight of a lower alcohol, wherein said shampoo composition has a viscosity of from about 400 mPa·s to about 3000 mPa·s.

* * * * *